(12) United States Patent
Moller et al.

(10) Patent No.: US 7,686,786 B2
(45) Date of Patent: Mar. 30, 2010

(54) DIAL-DOWN MECHANISM FOR WIND-UP PEN

(75) Inventors: Claus Schmidt Moller, Fredensborg (DK); Christian Peter Enggaard, Vejby (DK); Bo Radmer, Hillerød (DK); Tom Hede Markussen, Bagsværd (DK)

(73) Assignee: Novo Nordiks A/S, Bagsvaerd (DK)

( * ) Notice: Subject to any disclaimer, the term of this patent is extended or adjusted under 35 U.S.C. 154(b) by 287 days.

(21) Appl. No.: 11/665,486

(22) PCT Filed: Oct. 20, 2005

(86) PCT No.: PCT/EP2005/011285

§ 371 (c)(1),
(2), (4) Date: Oct. 11, 2007

(87) PCT Pub. No.: WO2006/045526

PCT Pub. Date: May 4, 2006

(65) Prior Publication Data

US 2008/0147005 A1    Jun. 19, 2008

(30) Foreign Application Priority Data

Oct. 21, 2004    (EP) .................................. 04077900

(51) Int. Cl.
*A61M 5/20* (2006.01)
(52) U.S. Cl. .................. 604/134; 604/135; 604/136
(58) Field of Classification Search ......... 604/131–139; 128/DIG. 12, DIG. 13
See application file for complete search history.

(56) References Cited

U.S. PATENT DOCUMENTS

| 5,104,380 | A | 4/1992 | Holman et al. |
| 6,221,046 | B1 | 4/2001 | Burroughs et al. |
| 2002/0173752 | A1 * | 11/2002 | Polzin .................. 604/233 |
| 2004/0199117 | A1 | 10/2004 | Giambattista et al. |
| 2005/0090782 | A1 * | 4/2005 | Marshall et al. ......... 604/211 |

FOREIGN PATENT DOCUMENTS

| EP | 0615762 A1 | 9/1994 |
| EP | 0937476 A2 | 8/1999 |
| WO | WO 02/053214 A1 | 7/2002 |
| WO | WO 2004054644 A1 * | 7/2004 |

* cited by examiner

*Primary Examiner*—Nicholas D Lucchesi
*Assistant Examiner*—Rebecca E Eisenberg
(74) *Attorney, Agent, or Firm*—Marc A. Began

(57) ABSTRACT

The present invention relates to a dial-down mechanism for an injection device comprising a torsion spring for assisting injection of a dose of medicament from the injection device, the dial-down mechanism comprising dial-up cam arranged to receive and engage with a dial-up key, wherein the dial-up cam and the dial-up key are adapted to, upon rotation of a dose setting member in a first direction, cooperate to strain the torsion spring of the injection device, and a dial-down cam arranged to receive and engage with a dial-down key, wherein the dial-down cam and the dial-down key are adapted to, upon rotation of the dose setting member in a second direction, cooperate to release the torsion spring of the injection device, the second rotation direction being opposite to the first rotation direction.

10 Claims, 5 Drawing Sheets

DIAL-DOWN MECHANISM FOR WIND-UP PEN

CROSS-REFERENCE TO RELATED APPLICATIONS

This application is a 35 U.S.C. § 371 national stage application of International Patent Application PCT/EP2005/011285 (published as WO 2006/045526), filed Oct. 20, 2005, which claimed priority of European Patent Application 04077900.1, filed Oct. 21, 2004; this application further claims priority under 35 U.S.C. § 119 of U.S. Provisional Application 60/626,270, filed Nov. 9, 2004.

FIELD OF THE INVENTION

The present invention relates to a dial-down mechanism for automatic wind-up pens. In particular, the present invention relates to integrated axial and radial dial-down mechanisms for wind-up pens.

BACKGROUND OF THE INVENTION

In known injection devices, such as wind-up pens, based on torsion springs, the use of dial-down mechanisms rely on that the user of the injection device applies a force to a rotatable dose setting member of the injection device. The force must be applied in order to axially withdraw the dose setting member a certain distance to release the dose setting member from a toothing mechanism or ratchet positioned within the body of the injection device. By releasing the dose setting member from this toothing mechanism the dose setting member can be reversed by rotation and set at a new and lower dose.

An example of a known wind-up pen applying a torsion spring may for example be found in U.S. Pat. No. 5,104,380. However, the pen suggested in U.S. Pat. No. 5,104,380 does not offer a dial-down mechanism. A dial-down mechanism is provided in WO 02/053214. However, the proposed solution in WO 02/053214 involves a linear spring.

It is a disadvantage of known torsion spring-based dial-down systems that the user must apply a force to withdraw the dose setting member a certain axial distance and, at the same time, adjust the angular position of the dose setting member. Especially for persons having reduced motoric skills or reduced finger strength, such as children, elderly people or disabled people this is a rather complicated procedure.

US 2004/199117 discloses a medication delivery pen including an arrangement where incorrect dosage settings may be corrected by a user via a dial-back feature that enables the user to reset the dose amount without expelling medication and without having to dial a dose knob to an extended, reset position. The medication delivery pen of US 2004/199117 is a so-called manual pen where the injection of a medicament from the pen is driven by a force purely provided by the user of the pen. Thus, the injection of a medicament is not assisted by any resilient member, such as a spring, and the dial-down arrangement disclosed in US 2004/199117 is not arranged to maintain a resilient member in a given strained position.

It is an object of the present invention to provide a dial-down mechanism for automatic wind-up pens. Automatic wind-up pens are here to be understood as pens having a resilient member, such as a spring, to assist injecting a medicament from an injection device.

SUMMARY OF THE INVENTION

The above-mentioned object is complied with by providing, in a first aspect, a dial-down mechanism for an injection device comprising a torsion spring for assisting injection of a dose of medicament from the injection device, the dial-down mechanism comprising dial-up cam arranged to receive and engage with a dial-up key, wherein the dial-up cam and the dial-up key are adapted to, upon rotation of a dose setting member in a first direction, cooperate to strain the torsion spring of the injection device, and a dial-down cam arranged to receive and engage with a dial-down key, wherein the dial-down cam and the dial-down key are adapted to, upon rotation of the dose setting member in a second direction, cooperate to release the torsion spring of the injection device, the second rotation direction being opposite to the first rotation direction.

Generally speaking the dial-down mechanism may be implemented as a radial dial-down mechanism or as an axial dial-down mechanism. In the radial dial-down mechanism the dial-down key or keys are arranged to move in the radial direction of the mechanism. This may also be the radial direction of the injection device. In the axial dial-down mechanism, the dial-down key or keys are arranged to move in the axial direction of the injection device.

Also it should be noted that the dial-up key or keys, and the dial-down key or keys may be different keys—i.e. physically separated keys. However, it may also be that the dial-up and dial-down key is constituted by the same key. Thus, it may be that the mechanism according to the present invention comprises only a single key which is used for both dial-up and dial down.

The dial-up and dial-down cams may be arranged as openings or indentations in an outer surface part of a disc-shaped cam member. The cam member may, alternatively, also be shaped as a substantially cylindrical member. In particular, the dial-up and dial-down cams may be arranged in a substantially plane surface part of the cam member. This substantially plane surface part may be substantially perpendicular to an axial direction of the disc or cylindrical shaped cam member. The cam member may be a hollow construction, or alternatively, the cam member may be a solid construction.

In both the radial and the axial mechanism, the dial-up cam may form a curved track, such as part of a circular, elliptical or parabolic track. The dial-down cam may form part of a V-shaped track, or alternative, it may have a rectangular shape.

The dial-down mechanism may comprise a first and a second dial-up cam. Furthermore, the dial-down mechanism may comprise a first and a second dial-up key, wherein the first dial-up key may be adapted to engage and cooperate with the first dial-up cam, and wherein the second dial-up key may be adapted to engage and cooperate with the second dial-up cam.

The dial-down mechanism may further comprise a first and a second dial-down cam, and a first and a second dial-down key. The first dial-down key may be adapted to engage and cooperate with the first dial-down cam, whereas the second dial-down key may be adapted to engage and cooperate with the second dial-down cam.

It may also be that the dial-up and dial-down cams form part of regions of the same track. Furthermore, the dial-up and dial-down keys may be constituted by the same key, said key being adapted to engage and cooperate with dial-up and dial-down cams of the same track.

In the axial mechanism, the dial-up and dial-down cams may be arranged as cams having an axial component parallel to an axial direction of the injection device. The dial-up and dial-down cams may be arranged on an outer and curved surface part of a substantially cylindrical cam member. This substantially cylindrical cam member may be the dose setting member of the injection device, or it may be a separate component cooperating with the dose setting member of the injection device.

In the axial mechanism, the dial-up cam may be substantially parallel to an axial direction of the injection device. In order to be able to release an associated ratchet from a toothing the dial-down cam may form an angle, such as around 45 degrees, to the dial-up cam.

In a second aspect, the present invention relates to an axially arranged dial-down mechanism for an injection device, the dial-down mechanism comprising a rotatable member adapted to be rotated when a dose to be injected from the injection device is set, the rotatable member comprising a dial-up cam and a dial-down cam, wherein the dial-up cam is adapted to receive and engage with a key of a ratchet of the injection device during dose setting during dial-up, and wherein the dial-down cam is adapted to receive and engage with the key during dial-down, wherein the dial-up cam is substantially parallel to an axial direction of the injection device.

In this second aspect of the present invention the dial-up and dial-down cams may form part of regions of the same track. The dial-up and dial-down keys may be constituted by the same key, said key being adapted to engage and cooperate with dial-up and dial-down cams of the same track.

In a third aspect, the present invention relates to a medication delivery device, such as a handheld medication delivery device, comprising a dial-down mechanism according to the first aspect of the present invention.

BRIEF DESCRIPTION OF THE DRAWINGS

The present invention will now be described in further details with reference to the accompanying figures, wherein.

Figure 1A:
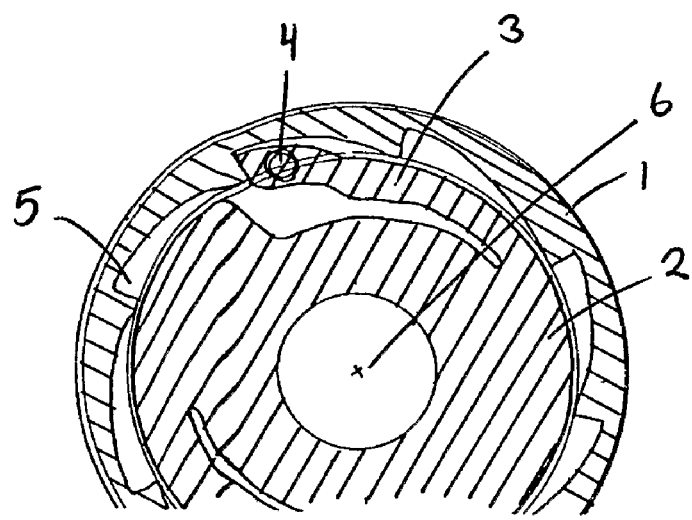
FIG. 1 shows the principle of a radial dial-up and dial-down mechanism where the keys on the flexible arm are used for both dial-up and dial-down.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

The dial-down mechanism according to the present invention may be implemented as an axial or a radial mechanism. Both of these mechanisms may be integrated into an injection device, such as an injection pen.

Figure 1B:
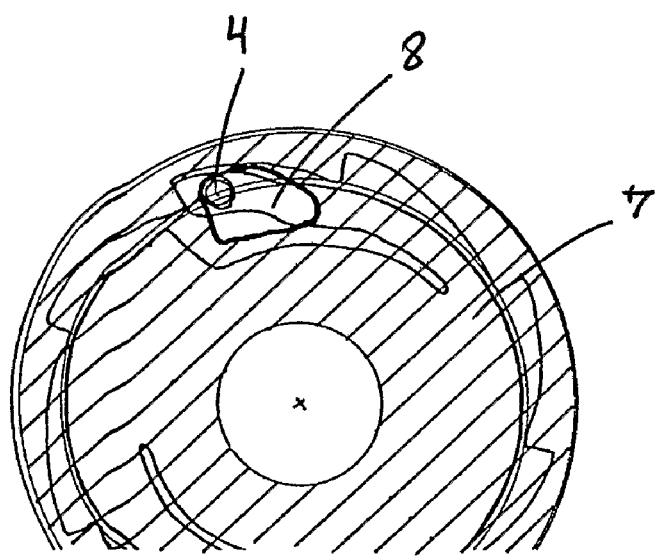

A radial solution is shown in FIG. 1. FIG. 1a shows a rotatable inner part 2 biased against a fixed outer part 1. The biasing force is provided by a torsion spring (not shown) in the counter-clockwise direction. The inner part 2, which is rotatable around a center axis 6, has one or more flexible arms 3 adapted to engage with the edges 5 in the fixed outer part 1. FIG. 1b shows the arrangement of FIG. 1a with a rotatable disc 7 (hatched region) placed on top of the inner part 2 and outer part 1. The disc 7 has an opening 8. The edges defining the opening 8 constitute dial-up and dial-down cams. A pick-up key 4 attached to, or integrated with, the flexible arm 3 operates as a cam follower when the disc 7 is rotated relative to the outer part 1.

The system illustrated in FIG. 1 is operated in the following manner:

When a dose is to be set (dial-up), the inner part 2 is rotated in the clockwise direction whereby the flexible arm 3 will move from one edge 5 to the neighboring edge or edges—depending on the angle of rotation. The inner part 2 is driven by disc 7—thus, when disc 7 is rotated the inner part 2 rotates with it. During rotation in the clockwise direction, the pick-up key 4 moves in and out along the radial direction.

When the disc 7 is rotated in the counter clockwise direction (dial-down direction) the pick-up key 4, and thereby the flexible arm 3, is lifted out of its engaging position with the edge 5 of the outer part 1. When the arm 3 is fully disengaged from the edge 5 the inner part 2 may be rotated in the counter clockwise direction relative to the outer part 1. It is a characteristic of the system shown in FIG. 1 that the pick-up key 4 is used for both dial-up (increasing a dose) and dial-down (resetting or reducing a dose).

It should be noted that the directions of rotation could be reversed so that dial-up is achieved by rotating the inner portion 2 in the counter clockwise direction. In such a configuration dial-down could be achieved by rotating disc 7 in the clockwise direction.

Figure 2:
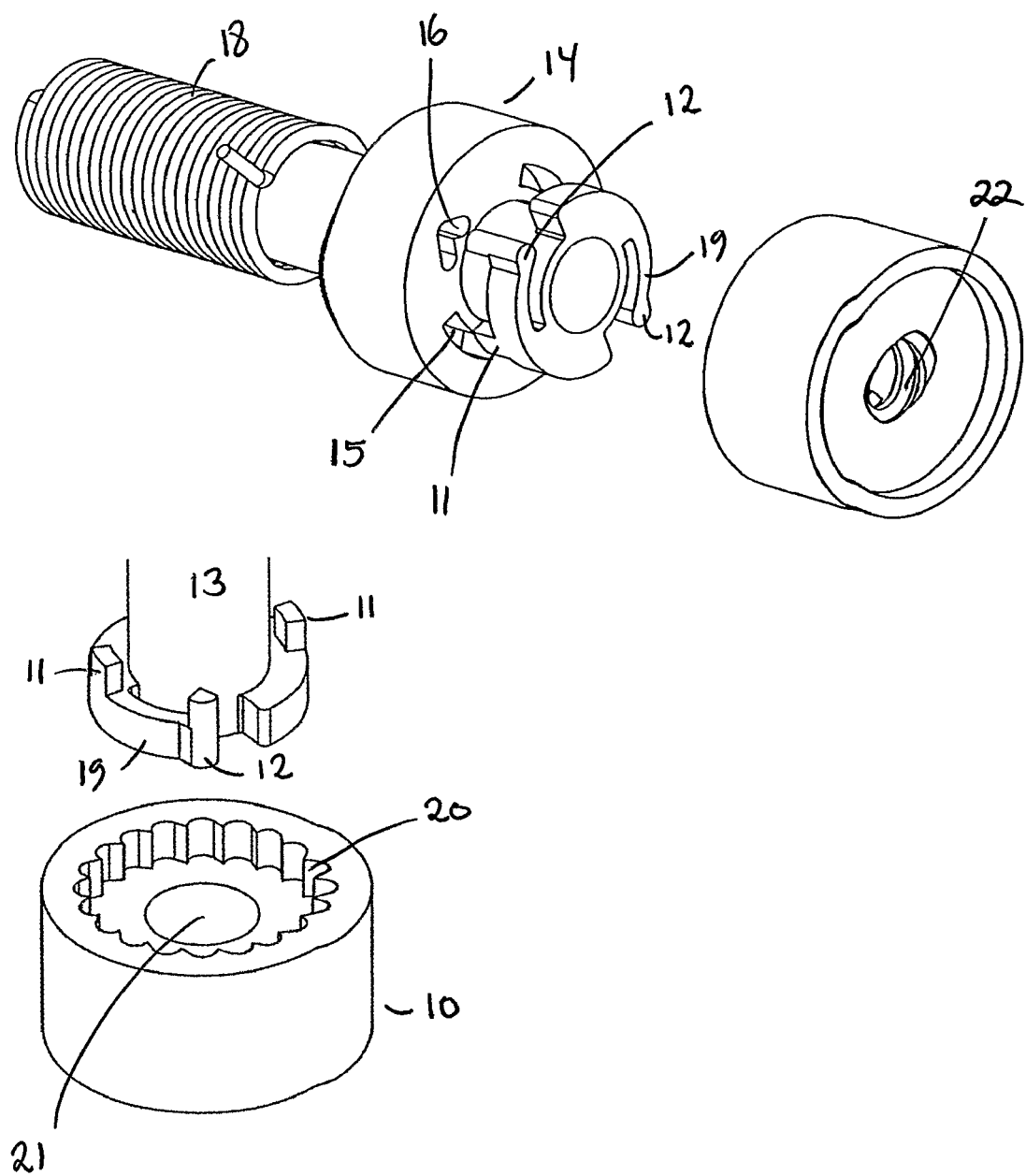
FIG. 2 shows a radial dial-up/dial down mechanism with separate keys for dial-up and dial-down.

FIG. 2 shows an exploded drawing of the radial embodiment of the dial-down mechanism according to the present invention. The main difference compared to the embodiment shown in FIG. 1 is that the embodiment of FIG. 2 applies different pick-up keys for dial-up (pick-up key 11) and dial-down (pick-up key 12). The dial-up key 11 engages with track 15 of the disc 14, whereas dial-down key 12 engages with track 16 of the disc 14. Tracks 15 and 16 are formed as through-going openings or indentations in a planar surface of the disc 14. The dial-up tracks 15 take the form of curved tracks whereas the dial-down tracks 16 are V-shaped. An obvious alternative to the V-shape is a rectangular shape. It should be noted that the general idea is that the dial-up tracks 15 should be capable of transferring a momentum to a torsion spring 18. In the same manner, the dial-down tracks 16 should be capable of releasing the dial-down keys (and thereby release energy) in case the disc 14 is rotated just a few degrees relative to the nut 10.

The dial-down keys 12 are integrated with the flexible arms 19. These arms are fabricated of a resilient material such as for example plastic. The flexible arms 19 with integrated dial-down keys 12 form an integral part of the ratchet 13. Thus, the ratchet including arms and dial-down keys may preferably be fabricated of the same material, such as of plastic. In order to bias the dial-down keys 12 against the teeth 20 of the nut 10 a torsion spring 18 is arranged coaxially with the ratchet 13. An opening 21 is provided in the center part of the nut 10. The side wall of this opening is provided with threads 22 which are adapted to engage with a threaded outer surface of a piston rod (not shown).

Figure 3:
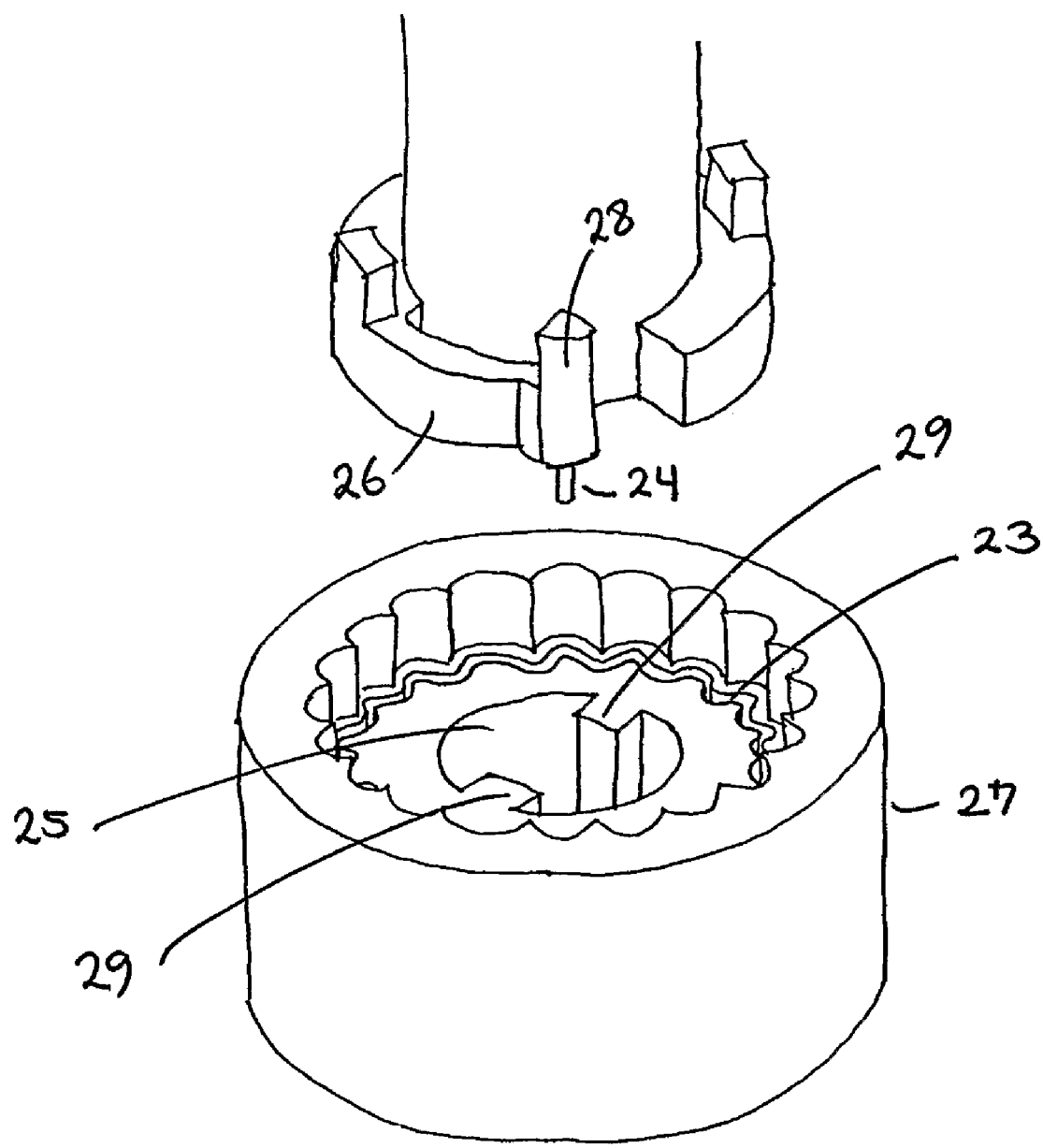
FIG. 3 shows a radial dial-up/dial down mechanism with separate keys for dial-up and dial-down where the movements of the dial-down key is determined by a track in the nut.

FIG. 3 shows another radial embodiment according to the present invention. In this embodiment, the movement of the arm 26 is controlled by a track 23 in the nut 27. The track 23 is engaged by the track/cam follower 24 which precisely guides the dial-down key 28 from one tooth to the neighboring tooth during dial-down. In contrast to FIG. 2 the opening 25 in the center of the nut 27 is provided with a track follower 29. This track follower is adapted to engage with a track in the outer surface of a piston rod (not shown).

Figure 4:
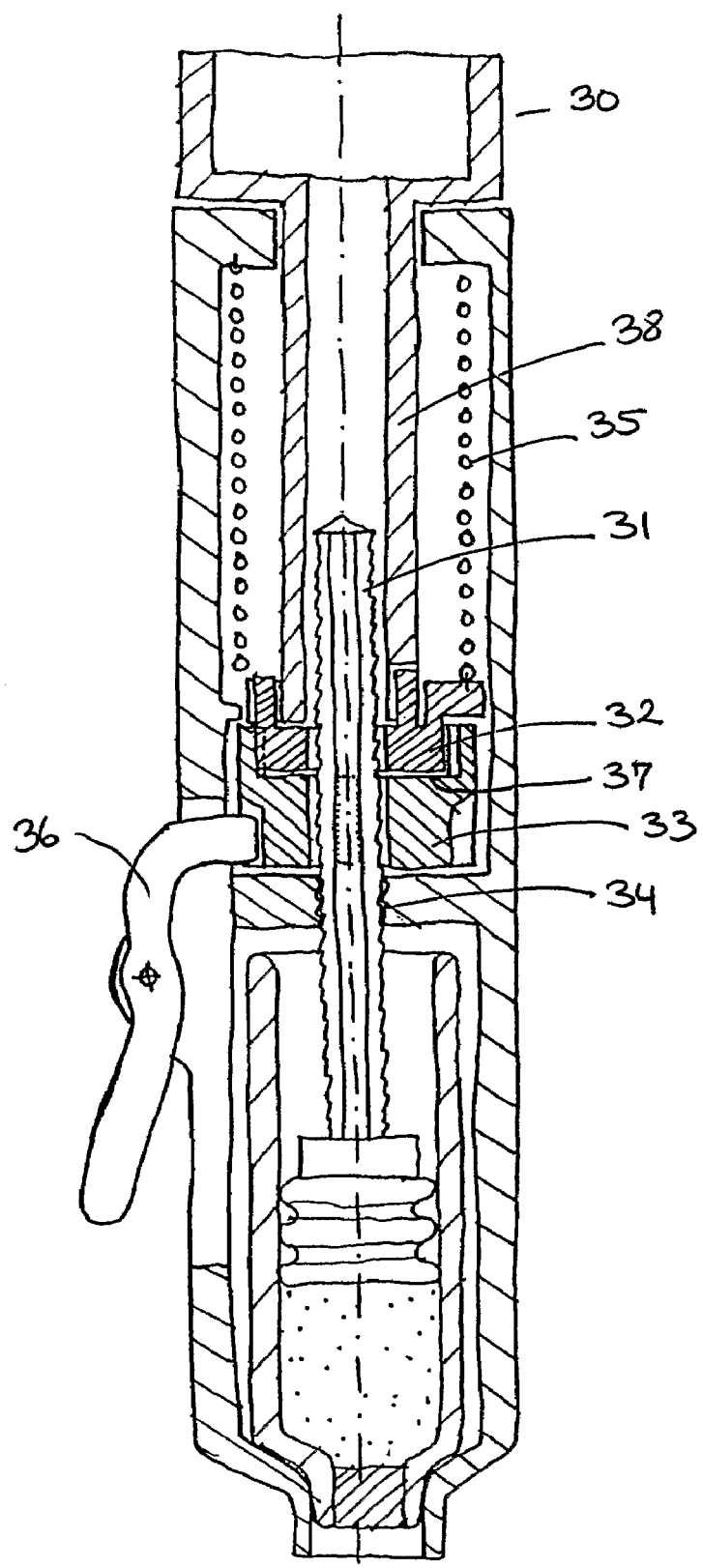
FIG. 4 shows an injection device having an integrated radial dial-down mechanism.

FIG. 4 shows an injection device having a radial dial-down mechanism according to the present invention. Among other components the injection device shown in FIG. 4 shows a dose setting member 30, a piston rod 31 having a threaded outer surface and a drive track arranged in the axial direction of the piston rod, a nut 32, a torsion spring 35, a drive member 33, the threaded portion 34 of the housing, a lease mechanism 36, a toothing mechanism 37, and ratchet 38.

A dose is set by rotating the dose setting member 30 and the nut 32 whereby the torsion spring 35 is strained. The dose setting member 30 is prevented from returning to its initial position due the toothing mechanism 37 positioned between the nut 32 and the drive member 33. In case the user wants to reduce a preset dose, the dose setting member 30 is simply rotated in the opposite direction. The interaction between ratchet 38 and nut 32 during dial-down is described in connection with FIG. 2.

Figure 5:
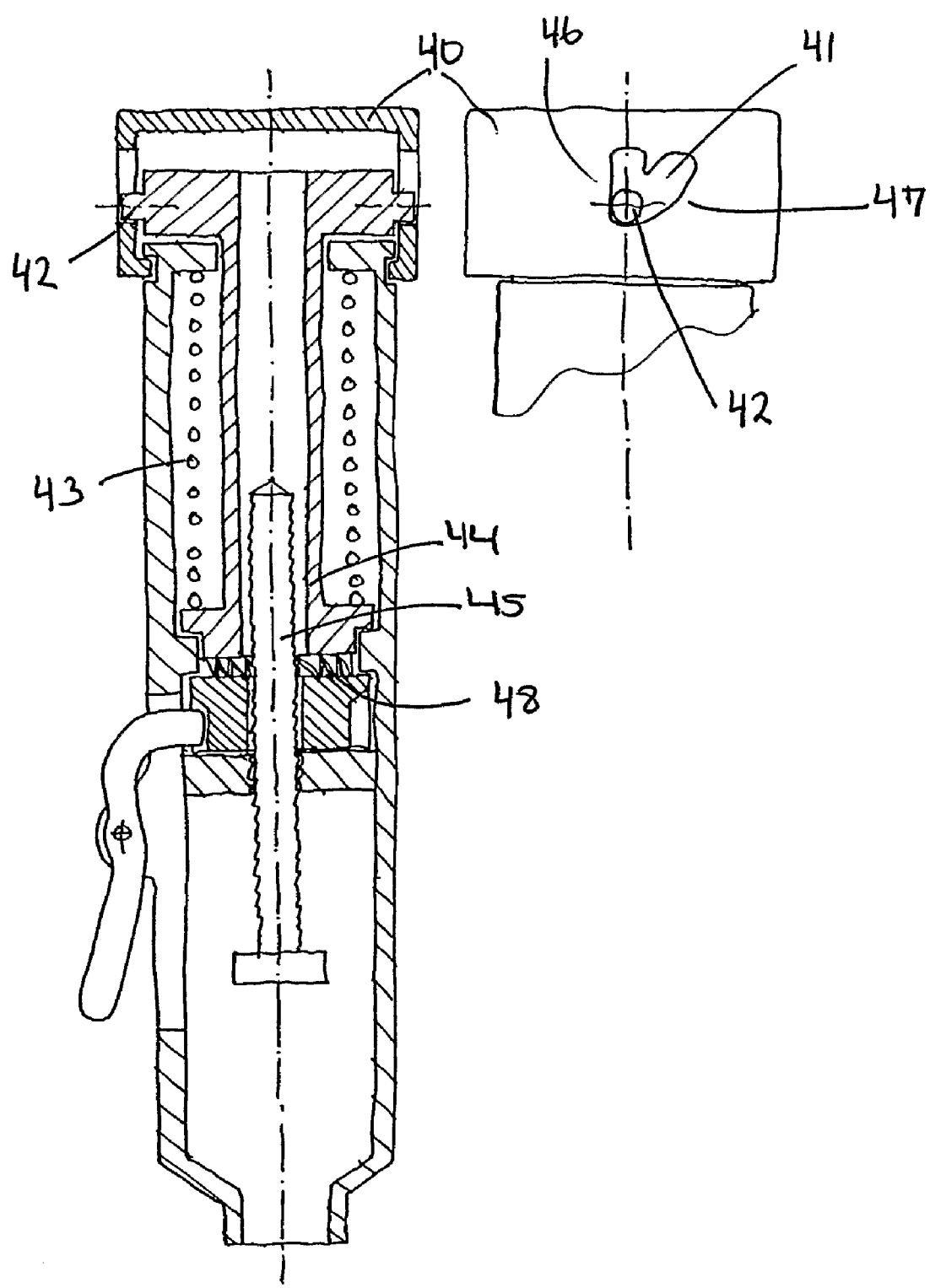
FIG. 5 shows an injection device having an integrated axial dial-down mechanism.

FIG. 5 shows an injection device having an axial dial-down mechanism according to the present invention. Among other components the injection device shown in FIG. 5 comprising a dose setting member 40, an opening 41 defining dial-up and dial-down cam surfaces, a cam follower 42, a torsion spring 43, a ratchet 44, and a piston rod 45. The general idea behind the axial dial-down mechanism is to use the torsion spring 43 to both drive and rotate the piston rod 45 and to ensure that the upper and lower parts of the toothing 48 remain together.

When a dose is to be set, the cam follower 42 engages with cam surface 46. As a result the torsion spring 43 is strained because the ratchet 44 is prevented from reversing due to the toothing 48. During dial-up the ratchet 44 will move up and down along cam surface 46 as the upper and lower parts of the toothing 48 rotate relative to each other. In case of dial-down the cam surface 47 will lift and thereby release the upper part of the toothing from the lower part of the toothing thereby the ratchet 44 is allowed to rotate an angle corresponding to one tooth.

The invention clamed is:

1. A dial-down mechanism for an injection device comprising a torsion spring (18) for assisting injection of a dose of medicament from the injection device, the dial-down mechanism comprising
   dial-up cam (15) arranged to receive and engage with a dial-up key (11), wherein the dial-up cam (15) and the dial-up key (11) are adapted to, upon rotation of a dose setting member in a first direction, cooperate to strain the torsion spring (18) of the injection device, and
   a dial-down cam (16) arranged to receive and engage with a dial-down key (12), wherein the dial-down cam (16) and the dial-down key (12) are adapted to, upon rotation of the dose setting member in a second direction, cooperate to release the torsion spring (18) of the injection device, the second rotation direction being opposite to the first rotation direction,
   wherein the dial-up and dial-down cams form part of regions of the same track,
   further comprising an arm wherein the dial-up and dial-down keys are both located on the same arm, said keys being adapted to engage and cooperate with dial-up and dial-down cams of the same track.

2. A dial-down mechanism according to claim 1, wherein the dial-up cam (15) forms part of a curved track.

3. A dial-down mechanism according to claim 2, wherein the curved dial-up cam (15) forms part of a circular, elliptical or parabolic track.

4. A dial-down mechanism according to claim 1 comprising a first and a second dial-up cam.

5. A dial-down mechanism according to claim 4 comprising a first and a second dial-up key, wherein the first dial-up key is adapted to engage and cooperate with the first dial-up cam, and wherein the second dial-up key is adapted to engage and cooperate with the second dial-up cam.

6. A dial-down mechanism according to claim 1, wherein the dial-down cam (16) forms part of a V-shaped track.

7. A dial-down mechanism according to claim 1 comprising a first and a second dial-down cam.

8. A dial-down mechanism according to claim 7 comprising a first and a second dial-down key, wherein the first dial-down key is adapted to engage and cooperate with the first dial-down cam, and wherein the second dial-down key is adapted to engage and cooperate with the second dial-down cam.

9. A medication delivery device comprising a dial-down mechanism according to claim 1.

10. A medication delivery device according to claim 9, wherein the medication delivery device is a handheld medication injection pen.

* * * * *